United States Patent
Brown et al.

(10) Patent No.: US 8,500,619 B2
(45) Date of Patent: Aug. 6, 2013

(54) APPARATUS AND METHOD FOR INDUCING VIBRATIONS IN A LIVING BODY

(75) Inventors: Peter S Brown, Palo Alto, CA (US); Claudio I. Zanelli, Sunnyvale, CA (US)

(73) Assignee: Onda Corporation, Sunnyvale, CA (US)

( * ) Notice: Subject to any disclaimer, the term of this patent is extended or adjusted under 35 U.S.C. 154(b) by 919 days.

(21) Appl. No.: 11/712,869

(22) Filed: Feb. 28, 2007

(65) Prior Publication Data

US 2007/0276217 A1 Nov. 29, 2007

Related U.S. Application Data

(63) Continuation of application No. 10/340,438, filed on Jan. 9, 2003, now abandoned, which is a continuation of application No. 10/007,755, filed on Oct. 25, 2001, now abandoned, which is a continuation of application No. 09/107,879, filed on Jun. 30, 1998, now abandoned.

(51) Int. Cl.
 *A61N 2/00* (2006.01)
(52) U.S. Cl.
 USPC .................................. 600/9; 600/12; 128/899
(58) Field of Classification Search
 USPC ................. 600/9, 12; 604/22; 606/169, 171; 128/899
 See application file for complete search history.

(56) References Cited

U.S. PATENT DOCUMENTS

| | | | |
|---|---|---|---|
| 3,043,309 A | 7/1962 | McCarthy | 600/12 |
| 3,358,676 A | 12/1967 | Frei et al. | 600/12 |
| 4,192,294 A | 3/1980 | Vasilevsky et al. | |
| 4,364,377 A | 12/1982 | Smith | 600/12 |
| 4,468,224 A | 8/1984 | Enzmann et al. | 604/247 |
| 4,545,368 A | 10/1985 | Rand et al. | |
| 4,554,929 A | 11/1985 | Samson et al. | |
| 4,569,347 A | 2/1986 | Frisbie | |
| 4,638,805 A | 1/1987 | Powell | |
| 4,920,954 A | 5/1990 | Alliger et al. | |
| 5,243,997 A | 9/1993 | Uflacker et al. | |
| 5,344,395 A | 9/1994 | Whalen et al. | 604/22 |
| 5,425,735 A | 6/1995 | Rosen et al. | 606/128 |
| 5,431,640 A | 7/1995 | Gabriel | 604/270 |
| 5,524,620 A | 6/1996 | Rosenschein | |
| 5,569,179 A | 10/1996 | Adrian | 604/22 |
| 5,626,593 A | 5/1997 | Imran | 606/159 |
| 5,681,260 A | 10/1997 | Ueda et al. | 600/114 |
| 5,728,062 A | 3/1998 | Brisken | 604/22 |
| 6,032,677 A | 3/2000 | Blechman et al. | 128/899 |

OTHER PUBLICATIONS

Search Report in a related PCT Application No. PCT/US99/14754, mailed Jun. 29, 1999.

*Primary Examiner* — Ruth S Smith
(74) *Attorney, Agent, or Firm* — Shirley L. Church Esq

(57) ABSTRACT

A medical device incorporating magnetic material is introduced into the body of a patient. A time varying magnetic field is generated externally of the patient's body and which is of sufficient strength to magnetically induce motion in the device, thereby causing the medical device to vibrate within the patient's body. The frequency and the amplitude of the magnetic field oscillations can be continuously varied to control the vibrations induced in the medical device.

37 Claims, 2 Drawing Sheets

APPARATUS AND METHOD FOR INDUCING VIBRATIONS IN A LIVING BODY

This application is a continuation application of U.S. patent application Ser. No. 10/340,438, filed Jan. 9, 2003, which is currently pending; which is a continuation of U.S. application Ser. No. 10/007,755, filed Oct. 25, 2001, abandoned; which is a continuation of U.S. application Ser. No. 09/107,879, filed Jun. 30, 1998, abandoned.

BACKGROUND OF THE INVENTION

The present invention relates to medical devices, and more particularly to a new method for inducing vibrations in such devices while they are disposed within a living body.

Vibrating medical devices, such as intravascular devices used in intravascular intervention, have been known in the art for some time and have been employed for a variety of uses. Such uses include, for example, facilitating the advancement of a catheter or guidewire through the vasculature to a target site by reducing the vessel wall friction encountered by the device, and breaking up thrombi and other intravascularly disposed masses either through direct mechanical contact, generation of ultrasound or pressure weaves to impact the mass, or enhancing the action of lysing agents.

One such prior art device is described in U.S. Pat. No. 5,243,997 to Uflacker et al., which discloses a vibrating device for a guidewire that consists of an electric motor mounted within a case and a clamp member mounted to the eccentric output shaft of the motor for securing and vibrating the guidewire. A physician can use this device for facilitating the introduction and advancement of a guidewire through a patient's vasculature. Alliger et al, in their U.S. Pat. No. 4,920,954 disclose a device for applying cavitation forces to a mass such as artery plaque through a guidewire vibrated by a transducer disposed within a handpiece that also supports the guidewire. The patent also discloses certain preferred modulus of elasticity and diameters for the guidewire.

U.S. Pat. No. 5,626,593 to Imran discloses a catheter with a solenoid disposed at its tip to vibrate a rounded tip and thus allow the catheter to more easily cross stenoses or lesions occluding a patient's vessel. The solenoid is supplied with current through electrical leads running along the catheter from its proximal end. A different approach is described, among others, by Rosen et al. in their U.S. Pat. No. 5,425,735, comprising a catheter with a shielded tip that can be a scraping or an impact element, and an energy source such as a laser with a fiber optic delivery system or a spark generator that creates repeated rapid vapor expansions adjacent the catheter tip. In this manner the vaporizing fluid causes the tip to undergo repeated pulsed movements, thereby enabling it to fracture or cut through an intravascular deposit.

Although the types of devices discussed above have met with varying degrees of success, they all suffer from some common limitations. Erstwhile, guidewires and catheters that transmit vibrating energy from an outside source to an intravascular site quickly lose effectiveness when they are disposed along a tortuous pathway or if they are highly flexible, and most of the vibrating energy is lost in the tissue surrounding the wire. In addition, some of the prior art reports that such guidewires have been known to break when sonic power was applied. Devices that carry the vibration generator at their distal tip for insertion into the patient's body are necessarily limited by the physical constraints imposed by such generators, which must be relatively large to create significant power, and thus preclude any meaningful use in certain applications such as neurovascular intervention. And although physical size is not a constraint with devices such as the Rosen pulsed energy catheter, such devices are relatively expensive, are somewhat difficult to use, and can generate significant heat with the attendant potential for tissue damage.

The acoustic catheter disclosed by Adrian in U.S. Pat. No. 5,569,179 employs a slightly different approach to achieve the same result, namely, generating acoustic energy at the distal tip of the catheter. This catheter is equipped at its distal end with a rotary-to-axial motion converter mechanism comprised of a first magnetic pole pair coupled to the end of a rotary shaft and a second pair of magnetic poles coupled to the proximal end of a non-rotating, reciprocal motion member that slides axially within the catheter. The two pairs of magnetic poles are located in close proximity such that as the first pair of poles is rotated, the second pair of poles is alternatingly attracted and repelled so as to induce reciprocating motion in the sliding member, which in turn generates acoustic energy that is emitted through the distal end of the catheter to ablate matter. This catheter therefore simply utilizes magnetic coupling as parts of its transducer mechanism, and suffers from the same limitations of energy losses due to friction and heat generation in to the surrounding tissue, as well as relative bulk and difficulty of deployment within the vasculature. In addition, this too is a relatively complex, uneconomical device.

Other prior art devices that employ ultrasound to break up thrombi have eliminated the use of an intravascular device completely, relying instead on ultrasounds generated externally of the patient's body and focused upon the target site. U.S. Pat. No. 5,524,620 to Rosenchein, for example, discloses a method whereby ultrasound generators such as piezoelectric crystals or spark type generators produce pulsed or continuous high intensity acoustic energy waves that are focused upon the desired area through what are described as conventional phased-array, time-array techniques. The preferred energy density at the focal area is disclosed to be in the 1 to 20 W/cm$^2$ range, and the acoustic lens is disposed in proximity to the skin of the patient about 5 to 30 cm from the thrombus. While it appears that favorable results have been obtained with this method, it presents the potential for overheating the tissue of the patient disposed between the acoustic lens and the thrombus, as well as the tissue surrounding the thrombus. In addition, the ultrasound generator is specified in the 10 to 50 KW range and produce as much as 100 W/cm$^2$, which is a rather large amount of energy to apply to a living body and would seem to limit the duration of treatment for this method. Reducing the amount of power applied will, of course, result in less energy reaching the target site, thus circumventing the main goal of this procedure.

In light of the above, it becomes apparent that there continues to be a need for a method to induce vibrations within a living body with a simple, efficient device that can be easily disposed within the body, such as an intravascular device that can navigate tortuous vasculature, poses greatly reduced risk of harm to the surrounding body tissue, and can be used for prolonged periods of time.

SUMMARY OF THE INVENTION

The present invention addresses the above mentioned needs by providing a method for generating vibrations within the body of a patient in a simple, economical manner with minimal risk and substantial flexibility. The method relies on equipment that is simple and economical to manufacture with a high degree of reliability. At its most basic, the method of the present invention entails the introduction of any one of a number of devices known in the art including, for example, intravascular devices such as guidewires or catheters, into a patient's body and positioning the device such that a predetermined portion of the device lies adjacent to the target site. The predetermined portion of the device incorporates a ferromagnetic or ferrimagnetic material, that is, a material that is susceptible to the attractive effects of magnetic fields. A pulsed magnetic field source, that is, a source that changes over time in magnitude and/or direction, of sufficient strength is disposed outside the patient's body in sufficient proximity to the intrabody device to induce motion in the device through the oscillating magnetic field that it emits. In this manner, a vibrating action is induced in the intrabody device of a frequency proportional to the frequency at which the magnetic source field pulsates.

By increasing or decreasing the frequency of the magnetic source field, the vibrating frequency of the intrabody device can be increased or decreased as well, and in this manner the intrabody device can be vibrated at sufficiently high frequencies to generate ultrasonic waves within the patient's body. By varying the strength of the magnetic field generated by the magnetic source, the amplitude of the mechanical vibrations generated by the intrabody device and their impact upon the surrounding tissue and other matter can be varied as well. Therefore, a physician employing the method of the present invention retains compete control over the procedure and can tailor the treatment to closely match the individual requirements of each patient.

In practice, the magnetic source is preferably an electromagnet connected to an alternating current source that causes the electromagnet to emit an oscillating magnetic field that changes polarity at a frequency matching the frequency of the alternating current source. To enhance the intrabody device's vibrating motion, a pair of such electromagnets disposed on opposite side of the patient's body and supplied by alternating current sources at out-of-phase voltages may be employed so that the electromagnets alternatingly attract the intrabody device in opposite directions. Alternatively, two or more electromagnets may be spaced around the intrabody device and each supplied with alternating current that is out of phase with the alternating current being supplied to the other electromagnets, so as to give rise to a three dimensionally oscillating magnetic field and affect the plane and direction of vibration of the magnetic material, thereby inducing three dimensional vibratory motion within the device.

The magnetic material is typically incorporated into the tip of the intrabody device, because the magnetic source acts upon the portion of the intrabody device that contains this material and thus the vibrating motion induced by the magnetic source is strongest at this portion. In a catheter incorporating such ferromagnetic or ferrimagnetic material, the material can also serve as the radiopaque marker at the tip of the catheter.

An intrabody device vibrated by the method of the present invention can be introduced intravascularly and used to break up thrombi or other masses through its mechanical vibrating motion or through waves generated by the intrabody device, or to enhance the action of lysing agents and other drugs by speeding up drug delivery and/or penetration and absorption into tissue. Such a device would be helpful in breaking up clots and emboli which cause ischemic stroke, myocardial infarction, deep vein thrombosis, pulmonary emboli, and other intravascular clots. In addition, the method of the present invention can be used to enhance the ability of an intravascularly introduced intrabody device to navigate the sometimes tortuous pathways of a patient's vasculature. The method of the present invention may also be used to induce vibrations in intravascularly disposed devices other than guidewires and catheters, such as stents and other permanently deployed devices for the purpose of reducing or eliminating clots that may have formed upon the device or otherwise affecting the body's response to such implants such as reducing vasospasms.

For the purpose of breaking up a thrombus through mechanical or ultrasonic action, it may be useful to equip the alternating current source driving the electromagnetic source with the ability to constantly vary the frequency, the amplitude, or both the frequency and the amplitude of the alternating current that it supplies. In this manner, the vibrations or ultrasounds emitted by the intrabody device can continuously sweep up and down over a predetermined range of frequencies so as to repeatedly impact the thrombus at its contemporaneous resonance frequency and thus greatly speed up the process of breaking up the thrombus. Because each thrombus is a heterogeneous structure, its resonance frequency range will vary according to its age, makeup and other variables. By continuously sweeping up and down over a range of frequencies, the intrabody device will repeatedly hit upon the resonance frequency of different portions of the thrombus regardless of how often or to what degree new clots are being formed, thereby greatly enhancing the efficiency end effectiveness with which the thrombi are dissolved without the need to somehow measure or gauge the various resonance frequencies of the thrombi present at any point in time.

DETAILED DESCRIPTION OF THE PREFERRED EMBODIMENTS

The present invention addresses the need for physicians and other medical personnel to be able to induce vibrations at a localized target site within a patient's body for any number of purposes, such as breaking up a thrombus or enhancing the action of medical drugs. The present invention provides a method for inducing vibrations in a manner that is simpler, safer, and more efficient and effective that previously known in the art.

Figure 1:
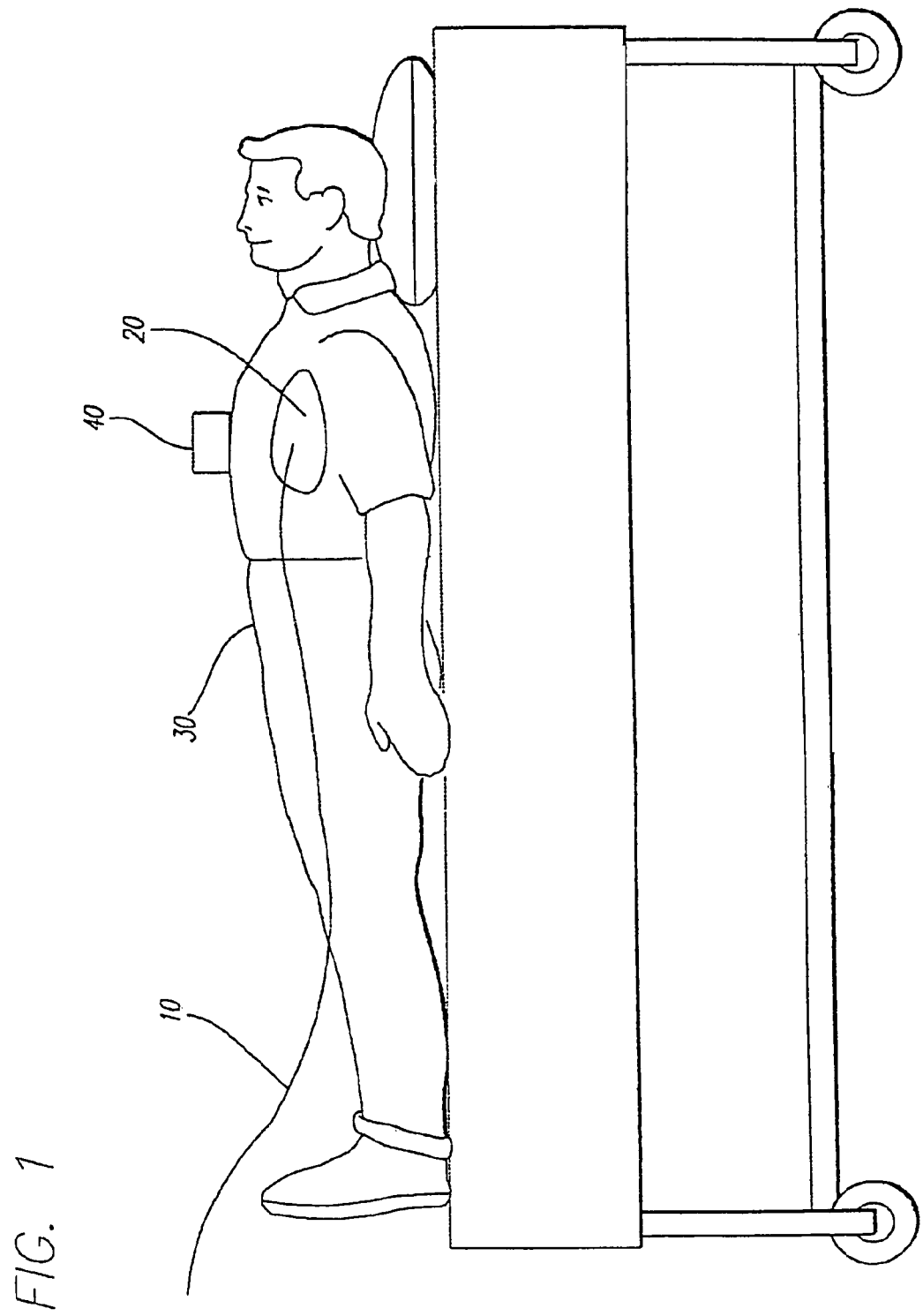
FIG. 1 is the side view of a patient with a guidewire inserted into his vasculature and a magnetic field generator positioned according to the method of the present invention to vibrate the tip of the guidewire

With reference to FIG. 1, the method of the present invention entails the placement of an object 10 to be vibrated in proximity to the target site 20 within the patient's body 30. The object may be an intravascular device introduced to the target site through the patient's vasculature, such as a guidewire (as shown in FIG. 1), a catheter, or a similar device. However, the method of the present invention may be employed equally efficaciously with other types of devices, including immobile devices such as stents, oils, clot traps, and filters, and motivated devices such as pumps. An object can be introduced into the patient's body through any number of presently known and practiced methods, such as are described in commonly-owned U.S. Pat. No. 4,468, 224 to Enzmann et al., U.S. Pat. No. 4,554,929 (RE33,911) to Samson et al., U.S. Pat. No. 4,569,347 to Frisbie, and U.S. Pat. No.

4,638,805 (RE35,176) to Powell, which are incorporated by reference herein in their entirety.

Regardless of the type, configuration, or disposition of the object 10 within the patient, any object to be vibrated by the method of the present invention must meet one basic requirement, namely that the object be comprised at least partially from a ferromagnetic or a ferrimagnetic material. Such magnetic material must be present in the object 10 in a sufficient proportion to allow the object to be influenced or motivated by a magnetic field. With the exception of catheters, the devices mentioned previously are typically constructed from metallic materials such as stainless steel and nickel titanium, and thus a wide variety of devices meet the requirement for incorporating magnetic material. For catheters to be used with the method of the present invention, magnetic material must be incorporated into the catheter's structure, preferably near the distal tip of the catheter. Because magnetic materials tend to be radiopaque, the magnetic material incorporated into the distal tip of catheter can also act as the marker relied upon by the physician to track the location of the catheter and the location of the vibration source within the patient's vasculature through currently known and used visualization systems. Furthermore, because the applied magnetic field of the present invention, as discussed below, acts solely upon the magnetic material, the physician is better able to localize the delivery of vibrations near the target site. In addition, disposing the magnetic material near or at the distal tip of a catheter increases the amplitude at which the catheter will vibrate in an oscillating magnetic field of a given strength because the plastic body of the catheter, which tends to dampen the vibratory motion experienced by the magnetic material, will be disposed on only one side of the magnetic material.

Once the object 10 has been disposed within the patient's body 30 at the target site 20, a pulsed magnetic field source 40 is disposed next to the patient in as close proximity to the intrabody object as practicable, as dictated by the location of the object within the patient. By a pulsed magnetic source is meant a magnetic field generator that generates an oscillating magnetic field, i.e., a field that repeatedly rises and falls in strength and that may or may not reverse direction from one cycle to the next. Thus, the magnetic field may be one that rises from a minimum amplitude (such as zero) to a maximum amplitude, decreases back to the minimum amplitude, then increases back again to the maximum amplitude in a repeated cycle. Alternatively, the magnetic field may be 'clipped' upon reaching the maximum amplitude to instantaneously fall back to the minimum amplitude. The magnetic field may also oscillate between opposite polarities, thus falling from a first maximum amplitude to zero, reversing direction and rising to a second maximum amplitude of opposite polarity to that of the first maximum amplitude, then falling back to zero and reversing direction again. These are but three examples, and the actual magnetic field source employed may produce an oscillating magnetic field having practically any type of amplitude curve, whether sinusoidal, saw-tooth, square, triangular, clipped sinusoidal, etc.

Figure 2:
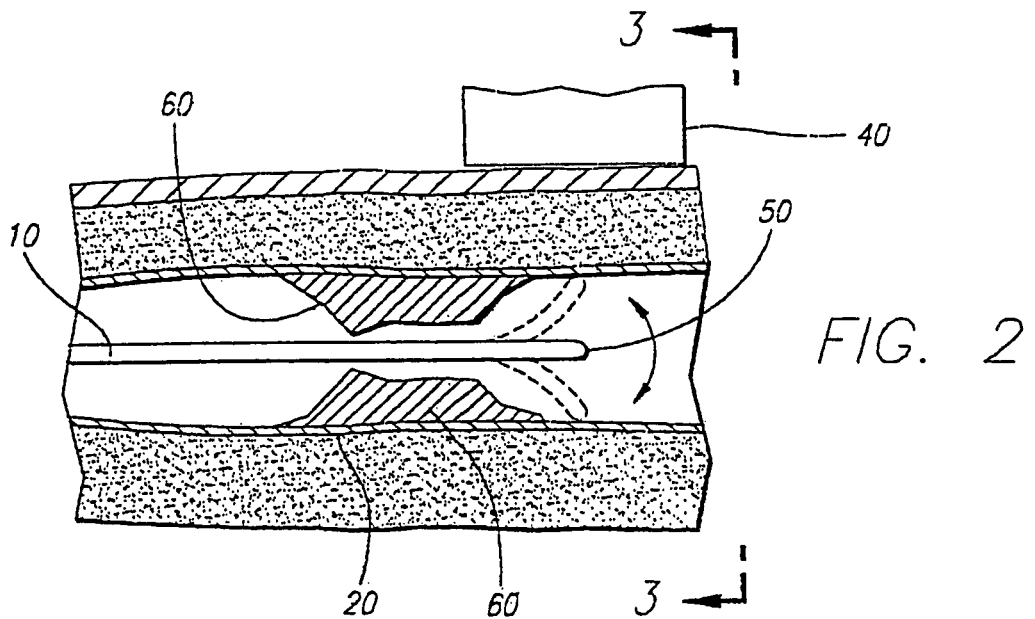
FIG. 2 is a sectional side view of the guidewire tip of FIG. 1 disposed within the vasculature of the patient and being vibrated by the magnetic field generator

Referring now to FIG. 2, the magnetic field generated must reach a maximum amplitude of sufficient strength to penetrate through the patient's body 30 to the target site 20 and motivate the magnetic object 10 disposed within by attracting the object, thus inducing an oscillating, or vibrating mechanical motion in the object in phase with that is the oscillating magnetic field produced by the pulsed magnetic source. The vibrating motion preferably will be concentrated at the tip 50 of the object 10 to enhance the amplitude of the vibrations and to allow the surgeon to more precisely localize the delivery of the vibrating mechanical energy to the immediate area of interest or other mass to be affected. The maximum amplitude that the applied magnetic field must reach is dependent upon a number of variables, including the size, shape, and weight of the intrabody object, the amount of magnetic material incorporated into the object, the distance and amount of tissue between the magnetic field source and the object, the frequency and wave shape of the oscillating magnetic field and, of course, the particular application for which the vibrations are being generated.

Similarly, the frequency at which the magnetic field oscillates must be adjusted to each individual application and thus, as an example, a guidewire being advanced into the vasculature of the patient may be vibrated in the kHz range to facilitate advancing the guidewire through the vasculature and then, upon reaching the target site of a thrombus, be vibrated in the MHZ range to break up the thrombus. In an alternative preferred method with particular application to breaking up thrombi, the frequency at which the magnetic field is oscillated, and thus the frequency at which the intrabody object is vibrated, is varied over a predetermined range to ensure that the various resonance frequencies of the target thrombi are each reached repeatedly. By vibrating a thrombus at its resonance frequency, which is the frequency at which the thrombus absorbs the most mechanical energy from the vibrations emanating from the intrabody object and exhibits the greatest response to it, the structure of the thrombus is shattered much more quickly than at other frequencies. By continuously varying the frequency of the oscillating field up and down over a predetermined range of frequencies, the particular resonance frequency of any thrombi at any given point in time will be reached repeatedly by the vibrating intrabody object, regardless of how often or to what degree the existing thrombi are being shattered and new ones being created. By causing such an up and down sweeping change in the frequency of the oscillating magnetic field, thrombi are eliminated in a much shorter period of time than achievable with a fixed-frequency vibrating device, thereby further enhancing the efficacy and the efficiency of the method of the present invention and, due to the much shortened treatment times, the safety and comfort of the patient.

The concept of breaking up thrombi and other tissue by vibrating the tissue over a range of frequencies is not limited solely to the method of the present invention, but may be used in conjunction with any other method of inducing intrabody vibrations, including any of the prior art methods and devices detailed previously as part of the background discussion. Thus, any vibrating device such as a laser vaporizer disposed at the distal tip of a catheter, or external ultrasound generators equipped with ultrasound focusing lenses, may be operated so as to generate ultrasounds, RF, electromagnetic, or other vibrations that vary continuously, or in discrete steps, over a predetermined range of frequencies and thus repeatedly vibrate the target tissue at its resonance frequency. The concept of applying vibrations of constantly varying frequency to break up tissue, a concept that is part of the present invention disclosed herein, can therefore be applied to previously known methods and devices to improve their performance and safety at relatively low cost and with relatively minor modifications to existing equipment.

From a practical point of view, continuously varying the frequency can be accomplished through the use of any one of a number of commonly known and available function or signal generators, such as the Hewlett Packard Model No. HP3314A, connected to a vibration generating device so as to control the frequency, the amplitude, or both the frequency and the amplitude of the vibration generated by the device. Thus, by way of example, a Model HP3314A signal generator may be electrically connected to a power audio amplifier such as the Precedent Series Model 1100A available from AB International, Inc., Roseville, Calif. The output of the amplifier may in turn be electrically connected to an electromagnet so as to cause the electromagnet to generate a magnetic field with an amplitude and/or frequency that oscillates according to the control signal generated by the HP signal generator. Finally, a magnetic object, such as for example a ferrous bead, needs to be internally disposed proximal to the target tissue to vibrate the tissue. The equipment may now be operated according to the method of the present invention by activating the signal generator and adjusting the signal thereby generated to the constraints of the desired function, which will in turn control the frequency and/or amplitude of the electric signal generated by the power amplifier and supplied to the electromagnet to generate a magnetic field that oscillates according to the same function. The magnetic field thus generated will magnetically attract the ferrous bead and thus induce vibrations therein that will impact the target tissue and whose frequency, magnitude and/or direction will likewise oscillate according to the function generated by the signal generator.

In a preferred application of the method of the present invention, the pulsed magnetic field source is in the form of an electromagnet supplied with electric alternating current. The electromagnet is comprised of a coil wound around a non-magnetic core such as plastic or aluminum. The alternating current flows through the coil to periodically magnetize the core, thus giving rise to a magnetic field that rises and falls in synchronicity with the frequency of the alternating current and is of an amplitude proportional to the amplitude of the alternating current. Therefore, by utilizing an electromagnet as the magnetic field source, the amplitude and frequency of the vibrations induced in the intrabody object can be varied, in keeping with the previous discussion, by varying the magnitude and the frequency, respectively, of the alternating current that is supplied to the electromagnet. Solely by way of example, experiments have been conducted utilizing a custom built electromagnet consisting of a coil comprising 80 turns of # 18 AWG copper wire wrapped around a plastic tubular core of plastic measuring 10 cm in diameter and 4 cm in length.

The equipment detailed above was connected as described to perform tests on a 4 mm diameter iron sphere in air, and measurements of the results obtained were taken using a F. W. Bell Model 4048 Gaussmeter. A magnetic field originating 10 mm from the sphere and oscillating sinusoidally at a frequency of 1.05 kHz with a flux density gradient of 50 Tesla/meter was established, causing the sphere to vibrate with a magnitude (in terms of displacement) of 0.0015 mm at a speed of 20 mm/second, thus absorbing approximately 0.1 mW of the transmitted power. The vibration amplitude achieved by the magnetic object is independent of its size, and is proportional to its magnetic permeability and the magnetic field, or flux density, gradient, and inversely proportional to the frequency at which the magnetic field oscillates. The energy absorbed by the object, on the other hand, is proportional to its mass. Therefore, initial experimental results appear to indicate that the preferred application of the method of the present invention includes relatively low magnetic field oscillating frequencies, high magnetic field flux density ($\mathcal{H}$) and density gradient ($\partial \mathcal{H}/\partial x$), and an object incorporating magnetic material having high magnetic permeability ($\mu$) and susceptibility ($\chi$).

The concept of constantly changing the vibrations emitted by the intrabody object may also be practiced by altering the amplitude, rather than the frequency, of the vibrations. In this manner, the vibrations generated by the object can repeatedly penetrate the surrounding tissue over a deeper to a shallower range. Such an approach could be employed when attempting to break up especially large thrombi to ensure that the entire mass of the thrombus is vibrated at least periodically while minimizing the amount of vibrational energy delivered to surrounding healthy tissue. In yet another alternative, both the frequency and the amplitude of the oscillating magnetic field may be varied over predetermined ranges, and may be synchronized such that the vibrations of highest amplitude are emitted at the highest frequencies, or alternatively at the lowest frequencies, or in any other relationship to the amplitude that the user of the present method may desire to practice. Thus, by way of example, the frequencies that affect surrounding tissue the most can be generated with the lowest amplitudes, and vice versa.

As alluded to previously, the method of the present invention can also be employed to assist the advancement of a guidewire or similar device through a patient's vasculature by applying the oscillating magnetic field to the device while it is being inserted through the vasculature, thereby reducing the friction encountered by the device against the vessel walls. In addition, the method of the present invention is not restricted to use with temporarily deployed intrabody devices, but can be applied with equal success to such permanent devices as expanded stents and other prostheses for the purpose of breaking up endothelial formations or clots, and filters for breaking up any clots trapped therein.

In another variation to the method of the present invention, two pulsed magnetic field sources may be placed on either side of the intrabody object and synchronized such that the magnetic fields emitted by the two sources oscillate out of phase but at equal frequencies. In this manner the two fields are always oriented in the same direction such that one of the magnetic sources exerts an attractive force upon the object out of phase with the other magnetic source. The advantage to such an arrangement resides in the fact that it creates no net force upon the object and thus does not stress the patient's tissue.

Figure 3:
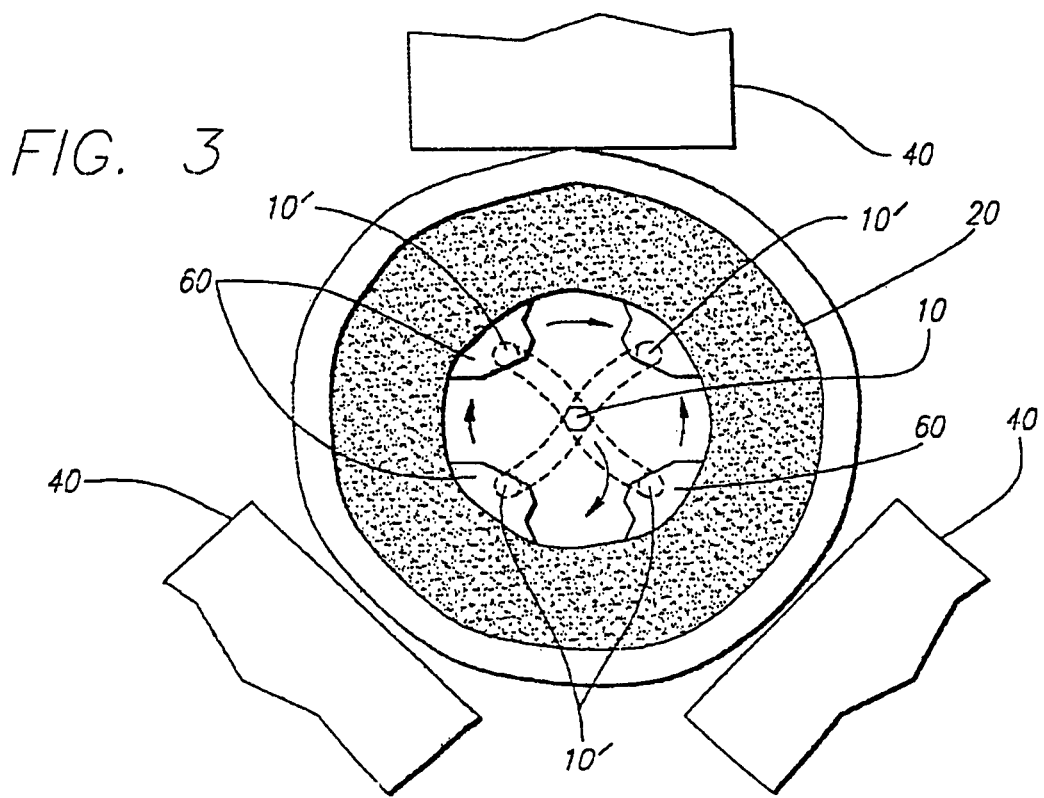
FIG. 3 is a front sectional view of the guidewire tip of FIG. 2 being vibrated three-dimensionally according to an alternative embodiment of the method of the present invention

With reference now to FIG. 3, the variation on the method of the present invention detailed above may be further enhanced by positioning two or more time-varying magnetic sources 40 around the intrabody object 10 spaced relative to one another, and optionally synchronizing the frequencies of the oscillating fields such that they lag one another by 60°, 90°, 120°, or any other amount, thereby inducing a three dimensional vibratory motion 10' in the intrabody object such as a circular motion, as opposed to a two-dimensional linear motion as would typically be induced by a single magnetic field source. In certain instances, such three dimensional vibrating motions 10' would help a guidewire navigate an especially tortuous pathway, or break up a large thrombus 60 with greater efficiency and expediency.

It must be understood, in light of the embodiment disclosed immediately above, that the method of the present invention is therefore not limited to inducing solely vibrating motion in an intrabody object, but rather any type of motion desired. Thus, in yet another exemplary embodiment, a rotating device such as a clot ablation tip or a motor or a blood micropump can be disposed within a patient and then induced to rotate at practically any desired speed by multiple pulsed magnetic sources disposed outside of the patient and spaced around the tip, and operated in the manner described previously. Alternatively, rotational motion can be induced by a single magnetic source that generates a constant magnetic field and is itself physically rotated, or even vibrated, thereby inducing rotational or vibrational motion in the intrabody device. In this manner, a wide variety of motivated intrabody devices can now be significantly reduced in size because there is not longer a need for a physical connection between the device and the driving means, such as through a shaft. Such devices can now be implanted for prolonged periods of time, perhaps even permanently, and be simply actuated periodically, as the need may arise, during a quick, painless, noninvasive procedure performed in a doctor's office.

It will therefore be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method of oscillating or vibrating tissue or other matter target site within a living body, comprising the steps of:
   providing an object into which a ferromagnetic or ferrimagnetic material has been rigidly incorporated to render the object susceptible to the attractive effects of at least one magnetic field;
   disposing the object at a specific location within the body, so that during application of a magnetic signal from at least one magnetic field generator, the object is in direct contact with the tissue or other matter target site to be oscillated or vibrated;
   disposing a magnetic field generator configured to be adjacent and external to the living body, with no physical connection to the object, where the magnetic field generator generates an oscillating magnetic field which induces a macroscopic mechanical oscillating or vibrating motion in the object; and
   adjusting at least one amplitude or frequency of an alternating current applied to the magnetic field generator, whereby macroscopic mechanical oscillation or vibration in the object is sufficient to permanently alter a physical structure of the tissue or other matter target site.

2. The method of claim 1, wherein the object is a guidewire, where the ferromagnetic or ferrimagnetic material is located at a distal end of the guidewire, and wherein the distal end of the guidewire is used to permanently alter a physical structure of the tissue.

3. The method of claim 1, wherein the object is a catheter, where the ferromagnetic or ferrimagnetic material is located at a distal end of the catheter, and wherein the distal end of the catheter is used to permanently alter a physical structure of the tissue.

4. The method of claim 1, wherein: the object includes a distal end and a proximal end; and the ferromagnetic or ferrimagnetic material is incorporated into the distal end of the object.

5. The method of claim 1, wherein the magnetic field generator comprises a first electromagnet, and wherein the step of adjusting at least one amplitude or frequency of an alternating current is sufficient to magnetically induce ultrasonic vibrations which are macroscopic in magnitude in the object.

6. The method of claim 5, wherein the frequency of the alternating current is adjusted, and wherein the frequency varies.

7. The method of claim 6, wherein the frequency of the alternating current varies over a predetermined range of frequencies.

8. The method of claim 6, wherein the frequency of the alternating current varies continuously over a predetermined range of frequencies.

9. The method of claim 6, wherein the frequency of the alternating current varies over a predetermined range of frequencies by repeatedly increasing from a minimum frequency to a maximum frequency and then decreasing from the maximum frequency to the minimum frequency.

10. The method of claim 6, wherein the frequency of the alternating current varies over a predetermined range of frequencies by repeatedly increasing from a minimum frequency to a maximum frequency.

11. The method of claim 6, wherein the frequency of the alternating current varies over a predetermined range of frequencies by repeatedly decreasing from a maximum frequency to a minimum frequency.

12. The method of claim 5, wherein an amplitude of the alternating current is adjusted, and wherein the amplitude varies.

13. The method of claim 12, wherein the amplitude of the alternating current varies over a predetermined range of amplitudes.

14. The method of claim 12, wherein the amplitude of the alternating current varies continuously over a predetermined range of amplitudes.

15. The method of claim 5, wherein the frequency and the amplitude of the alternating current vary during application of the method to oscillate and vibrate tissue.

16. The method of claim 15, wherein the frequency and amplitude of the alternating current vary over a predetermined range of frequencies and amplitudes, respectively.

17. The method of claim 15, wherein the frequency and the amplitude of the alternating current vary continuously over a predetermined range of frequencies and amplitudes, respectively.

18. The method of claim 15, wherein the frequency and the amplitude of the alternating current vary in a predetermined relationship to one another over a predetermined range of frequencies and amplitudes, respectively.

19. The method of claim 5, wherein the field generator includes a second electromagnet which is disposed opposite from the first electromagnet, and the second electromagnet is supplied with alternating current at an equal frequency and out-of-phase voltage to the alternating current supplied to the first electromagnet.

20. The method of claim 5, wherein the field generator includes two or more additional electromagnets which are spaced around the object, and alternating current is supplied to each additional electromagnet, wherein each alternating current has a frequency equal to that of the alternating current supplied to the first electromagnet and has a voltage out of phase with the voltage of the alternating current supplied to the first electromagnet and out of phase with one another.

21. A method of breaking down tissue or other matter within a living body, comprising the steps of:
   providing an object into which a ferromagnetic or ferrimagnetic material has been rigidly incorporated to render the object susceptible to the attractive effects of at least one magnetic field;
   placing the object in direct contact with or adjacent to the tissue or other matter, so that during application of a magnetic signal from at least one pulsating magnetic source, the object is in direct contact with the tissue or other matter; and
   applying a magnetic signal from at least one pulsating magnetic source with no physical connection to the object, to cause the object to make an oscillating or vibrating motion which permanently alters a physical structure of the tissue or other matter, and wherein the frequency of the magnetic signal is repeatedly varied to oscillate or vibrate the object.

22. The method of claim 21, wherein the step of varying the frequency of the magnetic signal comprises varying the frequency over a predetermined range of frequencies.

23. The method of claim 21, comprising the additional step of repeatedly varying the amplitude of the magnetic signal.

24. The method of claim 23, wherein the step of varying the amplitude of the magnetic signal comprises repeatedly varying the amplitude over a predetermined range of amplitudes.

25. The method of claim 23, wherein the step of varying the amplitude of the magnetic signal comprises repeatedly varying the amplitude in a predetermined relationship to the varying frequency of the magnetic signal.

26. The method of claim 25, wherein the relationship is a proportional relationship.

27. The method of claim 25, wherein the relationship is an inversely proportional relationship.

28. A method of breaking down tissue or other matter target site within a living body, comprising the steps of:
    providing an object into which a ferromagnetic or ferrimagnetic material has been rigidly incorporated to render the object susceptible to the attractive effects of at least one magnetic field;
    disposing the object at a specific location within the body in direct contact with or adjacent to the tissue or other matter target site, so that during generation of an oscillating magnetic field, the object is in contact with the tissue or other matter target site;
    disposing a magnetic field generator configured to be adjacent and external to the living body, with no physical connection to the object, where the magnetic field generator generates an oscillating magnetic field which induces a macroscopic mechanical or oscillating or vibrating motion in the object; and
    adjusting at least one amplitude or frequency of an alternating current applied to the magnetic field generator to generate a magnetic signal, whereby macroscopic mechanical oscillation or vibration in the object is sufficient to permanently alter a physical structure of the tissue or other matter site.

29. The method of claim 28, wherein the amplitude of the magnetic signal is varied over a predetermined range of amplitudes.

30. An assembly for generating vibrations within a living body, comprising:
    an object into which a ferromagnetic or ferrimagnetic material has been rigidly incorporated to render the object susceptible to the attractive effects of at least one magnetic field, where the object is configured to be positioned in direct contact with or adjacent to a tissue or other matter target site within a living body, so that during application of a magnetic field to a magnetic field generator, the object is in direct contact with the tissue or other matter;
    a magnetic field generator configured to be disposed adjacent and external to the living body, with no physical connection to the object, where the magnetic field generator is useful for generating an oscillating magnetic field which induces macroscopic mechanical oscillating or vibrating motion in the object; and
    a device which enables adjustment of at least one of the amplitude or frequency of an alternating current applied to the magnetic field generator, whereby a physical structure of the tissue or other matter target site is permanently altered.

31. The assembly of claim 30, wherein the object is a guidewire which includes the ferromagnetic or ferrimagnetic material at a distal end of the guidewire, and wherein the distal end of the guidewire is used to permanently alter a physical structure of the tissue.

32. The assembly of claim 30, wherein the object is a catheter which includes the ferromagnetic or ferrimagnetic material at a distal end of the catheter, and wherein the distal end of the catheter is used to permanently alter a physical structure of the tissue.

33. The assembly of claim 30, wherein:
    the object includes a distal end and a proximal end; and
    the ferromagnetic or ferrimagnetic material is incorporated into the distal end portion of the object.

34. The assembly of claim 30, wherein the magnetic field generator comprises a first electromagnet for generating a first oscillating magnetic field to induce macroscopic motion in the object.

35. The assembly of claim 34, wherein the alternating current is of a frequency sufficient to cause the first electromagnet to oscillate the first magnetic field at a frequency sufficient to magnetically induce ultrasonic vibrations which are macroscopic in magnitude in the object.

36. The assembly of claim 34, further comprising a second electromagnet configured to be disposed adjacent to the body and opposite from the first electromagnet, wherein the second electromagnet is supplied with alternating current at an equal frequency and out-of-phase voltage to the alternating current supplied to the first electromagnet, for generating a second magnetic field oscillation out-of-phase with the first magnetic field.

37. The assembly of claim 34, further comprising two or more additional electromagnets configured to be disposed adjacent to the body and spaced around the object, wherein the two or more additional electromagnets are supplied with alternating currents having a frequency equal to that of the alternating current supplied to the first electromagnet, and wherein the two or more additional electromagnets have voltages out of phase with the voltage of the alternating current supplied to the first electromagnet and to one another, for generating magnetic fields oscillating out of phase with each other, to magnetically induce three-dimensional macroscopic vibrating motion in the object.

* * * * *

UNITED STATES PATENT AND TRADEMARK OFFICE
CERTIFICATE OF CORRECTION

PATENT NO. : 8,500,619 B2  
APPLICATION NO. : 11/712869  
DATED : August 6, 2013  
INVENTOR(S) : Peter S. Brown and Claudio I. Zanelli Page 1 of 3

It is certified that error appears in the above-identified patent and that said Letters Patent is hereby corrected as shown below:

In the Specification

Column 1, lines 16 – 25 should read:
 "Vibrating medical devices, such as intravascular devices used in intravascular intervention, have been known in the art for some time and have been employed for a variety of uses. Such uses include, for example, facilitating the advancement of a catheter or guidewire through the vasculature to a target site by reducing the vessel wall friction encountered by the device, and breaking up thrombi and other intravascularly disposed masses either through direct mechanical contact, generation of ultrasound or pressure waves to impact the mass, or enhancing the action of lysing agents."

Column 2, lines 5 – 25 should read:
 "The acoustic catheter disclosed by Adrian in U.S. Patent No. 5,569,179 employs a slightly different approach to achieve the same result, namely, generating acoustic energy at the distal tip of the catheter. This catheter is equipped at its distal end with a rotary-to-axial motion converter mechanism comprised of a first magnetic pole pair coupled to the end of a rotary shaft and a second pair of magnetic poles coupled to the proximal end of a non-rotating, reciprocal motion member that slides axially within the catheter. The two pairs of magnetic poles are located in close proximity such that as the first pair of poles is rotated, the second pair of poles is alternatingly attracted and repelled so as to induce reciprocating motion in the sliding member, which in turn generates acoustic energy that is emitted through the distal end of the catheter to ablate matter. This catheter therefore simply utilizes magnetic coupling as parts of its transducer mechanism, and suffers from the same limitations of energy losses due to friction and heat generation into the surrounding tissue, as well as relative bulk and difficulty of deployment within the vasculature. In addition, this too is a relatively complex, uneconomical device."

Column 2, lines 26 – 49 should read:
 "Other prior art devices that employ ultrasound to break up thrombi have eliminated the use of an intravascular device completely, relying instead on ultrasounds generated externally of the patient's body and focused upon the target site. U.S. Patent No. 5,524,620 to Rosenchein, for example, Signed and Sealed this  
Twentieth Day of May, 2014

Michelle K. Lee  
*Deputy Director of the United States Patent and Trademark Office*

CERTIFICATE OF CORRECTION (continued)
U.S. Pat. No. 8,500,619 B2 discloses a method whereby ultrasound generators such as piezoelectric crystals or spark type generators produce pulsed or continuous high intensity acoustic energy waves that are focused upon the desired area through what are described as conventional phased-array, time-array techniques. The preferred energy density at the focal area is disclosed to be in the 1 to 20 W/cm2 range, and the acoustic lens is disposed in proximity to the skin of the patient about 5 to 30 cm from the thrombus. While it appears that favorable results have been obtained with this method, it presents the potential for overheating the tissue of the patient disposed between the acoustic lens and the thrombus, as well as the tissue surrounding the thrombus. In addition, the ultrasound generator is specified to operate in the 10 to 50 KW range and produce as much as 100 W/cm2, which is a rather large amount of energy to apply to a living body and would seem to limit the duration of treatment for this method. Reducing the amount of power applied will, of course, result in less energy reaching the target site, thus circumventing the main goal of this procedure."

Column 4, lines 31 – 40 should read:
"FIGURE 1 is the side view of a patient with a guidewire inserted into his vasculature and a magnetic field generator positioned according to the method of the present invention to vibrate the tip of the guidewire.
FIGURE 2 is a sectional side view of the guidewire tip of FIG. 1 disposed within the vasculature of the patient and being vibrated by the magnetic field generator.
FIGURE 3 is a front sectional view of the guidewire tip of FIG. 2 being vibrated three-dimensionally according to an alternative embodiment of the method of the present invention."

Column 4, lines 45 – 52 should read:
"The present invention addresses the need for physicians and other medical personnel to be able to induce vibrations at a localized target site within a patient's body for any number of purposes, such as breaking up a thrombus or enhancing the action of medical drugs. The present invention provides a method for inducing vibrations in a manner that is simpler, safer, and more efficient and effective than previously known in the art."

Column 4, lines 53 – 67 continuing to Column 5, lines 1 – 2 should read:
"With reference to Fig. 1, the method of the present invention entails the placement of an object 10 to be vibrated in proximity to the target site 20 within the patient's body 30. The object may be an intravascular device introduced to the target site through the patient's vasculature, such as a guidewire (as shown in Fig. 1), a catheter, or a similar device. However, the method of the present invention may be employed equally efficaciously with other types of devices, including immobile devices such as stents, coils, clot traps, and filters, and motivated devices such as pumps. An object can be introduced into the patient's body through any number of presently known and practiced methods, such as are described in commonly-owned U.S. Patent Nos. 4,468,224 to Enzmann et al., 4,554,929 (RE33,911) to Samson et al., 4,569,347 to Frisbie, and 4,638,805 (RE35,176) to Powell, which are incorporated by reference herein in their entirety."

Column 6, lines 10 – 40 should read:
"Similarly, the frequency at which the magnetic field oscillates must be adjusted to each individual application and thus, as an example, a guidewire being advanced into the vasculature of the patient may be vibrated in the kHz range to facilitate advancing the guidewire through the vasculature and then, upon reaching the target site of a thrombus, be vibrated in the MHz range to break up the thrombus. In an alternative preferred method with particular application to breaking up thrombi, the frequency at which the magnetic field is oscillated, and thus the frequency at which the intrabody object is vibrated, is varied over a predetermined range to ensure that the various resonance frequencies of the target thrombi are each reached repeatedly. By vibrating a thrombus at its resonance frequency, which is the frequency at which the thrombus absorbs the most mechanical energy from the vibrations emanating from the intrabody object and exhibits the greatest response to it, the structure of the thrombus is shattered much more quickly than at other frequencies. By continuously varying the frequency of the oscillating field up and down over a predetermined range of frequencies, the particular resonance frequency of any thrombi at any given point in time will be reached repeatedly by the vibrating intrabody object, regardless of how often or to what degree the existing thrombi are being shattered and new ones being created. By causing such an up and down sweeping change in the frequency of the oscillating magnetic field, thrombi are eliminated in a much shorter period of time than achievable with a fixed-frequency vibrating device, thereby further enhancing the efficacy and the efficiency of the method of the present invention and, due to the much shortened treatment times, the safety and comfort of the patient."

Column 8, lines 53 – 67 continuing to Column 9, lines 1 – 8 should read:
"It must be understood, in light of the embodiment disclosed immediately above, that the method of the present invention is therefore not limited to inducing solely vibrating motion in an intrabody object, but rather any type of motion desired. Thus, in yet another exemplary embodiment, a rotating device such as a clot ablation tip or a motor or a blood micropump can be disposed within a patient and then induced to rotate at practically any desired speed by multiple pulsed magnetic sources disposed outside of the patient and spaced around the tip, and operated in the manner described previously. Alternatively, rotational motion can be induced by a single magnetic source that generates a constant magnetic field and is itself physically rotated, or even vibrated, thereby inducing rotational or vibrational motion in the intrabody device. In this manner, a wide variety of motivated intrabody devices can now be significantly reduced in size because there is no longer a need for a physical connection between the device and the driving means, such as through a shaft. Such devices can now be implanted for prolonged periods of time, perhaps even permanently, and be simply actuated periodically, as the need may arise, during a quick, painless, noninvasive procedure performed in a doctor's office."